US00PP16494P2

(12) United States Plant Patent
Bradford

(10) Patent No.: US PP16,494 P2
(45) Date of Patent: May 2, 2006

(54) NECTARINE TREE NAMED 'GRAND BRIGHT'

(50) Latin Name: *Prunus persica*
Varietal Denomination: Grand Bright

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 121 days.

(21) Appl. No.: 11/029,691

(22) Filed: Jan. 6, 2005

(51) Int. Cl.
*A01H 5/00* (2006.01)

(52) U.S. Cl. ..... Plt./190
(58) Field of Classification Search ..... Plt./190
See application file for complete search history.

(56) References Cited

U.S. PATENT DOCUMENTS

PP7,918 P 7/1992 Bradford
PP11,952 P2 * 6/2001 Bradford ..... Plt./190
PP12,011 P2 * 7/2001 Gerawan ..... Plt./190
PP13,792 P2 * 5/2003 Serimian et al. ..... Plt./190
2003/0014789 P1 * 1/2003 Serimian et al. ..... Plt./190

* cited by examiner

*Primary Examiner*—Anne Marie Grunberg
*Assistant Examiner*—W. C. Haas

(57) ABSTRACT

The present invention relates to a nectarine tree, *Prunus persica,* and more particularly to a new and distinct variety broadly characterized by a large size, vigorous, hardy, self-fertile, productive and regular bearing tree. The fruit matures under the ecological conditions described in mid July, with first picking on Jul. 14, 2003. The fruit is uniformly large in size, mildly acidic and sweet in flavor, globose in shape, clingstone in type, firm in texture, yellow in flesh color, and mostly red in skin color. The variety was developed as a first generation cross using 'Ruby Diamond' (U.S. Plant Pat. No. 7,918) yellow flesh nectarine as the selected seed parent and an unnamed yellow flesh clingstone nectarine as the selected pollen parent.

1 Drawing Sheet

Latin name: *Prunus persica.*
Varietal denomination: 'Grand Bright'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'Grand Bright'. The present variety was hybridized by me in 1997, grown as a seedling on its own root in my greenhouse, and transplanted to a cultivated area of my experimental orchard at Bradford Farms near Le Grand, Calif. in Merced County (San Joaquin Valley). The variety was developed as a first generation cross using 'Ruby Diamond' (U.S. Plant Pat. No. 7,918) yellow flesh nectarine as the selected seed parent and an unnamed yellow flesh clingstone nectarine (unpatented) as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its selected seed parent, 'Ruby Diamond' (U.S. Plant Pat. No. 7,918) nectarine by producing nectarines that are mostly red in skin color, yellow in flesh color, mildly acidic and sweet in flavor, and nearly globose in shape but is distinguished therefrom by producing nectarines that are clingstone instead of freestone, that are much larger in size, and that mature about seven days later.

SUMMARY OF VARIETY in summary, the present variety is characterized by a large size, vigorous, hardy, self-fertile, productive and regular bearing tree. The fruit matures under the ecological conditions described in mid July, with first picking on Jul. 14, 2003. The fruit is uniformly large in size, mildly acidic and sweet in flavor, globose in shape, clingstone in type, firm in texture, yellow in flesh color, and mostly red in skin color.

DRAWING

The accompanying photograph consists of four whole fruits positioned to exhibit the characteristics of the skin color and form, one fruit divided transversely to the suture plane to reveal the flesh, a dried stone, typical leaves, and an inset depicting several flowers, a typical petal, and flower buds at various stages.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 17, 2003, on the original tree during its sixth growing season. All major color code designations are by reference to the Inter-Society Color Council, National Bureau of Standards. Common color names are also used occasionally.

TREE

Size: Large, reaching a height of 14' [4.27 m.] and a spread of 10' [3.05 m.] after six growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Trunk:

*Size.*—Medium, with a maximum diameter of 4 5/8" [117.5 m] after the sixth growing season.

*Texture.*—Shaggy.

*Bark color.*—Moderate brown [58. m.Br] with Grayish yellowish brown [80. gy.yBr] variegation.

*Lenticels.*—Approximate Number Per Square Inch: 10. Color: Moderate orange yellow [71. m.OY]. Typical Size: 3/16" to 7/16 [4.8–11.1 mm.]. Shape: Eye-shaped to elongated.

Branches:

*Size.*—Diameter of limb is 2½" [64 mm.] measured 12" above the crotch, typical of *Prunus persica,* and dependent upon cultural practices and climatic conditions.

*Texture.*—Shaggy.

*Color.*—1st Year Wood Topside: Grayish red [19. gy.R]. 1st Year Wood Underside: Brilliant yellow green [116. brill.YG]. Older Wood: Strong yellowish brown [74. s.yBr].

*Lenticels.*—Number Per Square Inch: More than 80 on second year wood. Color: Light orange yellow [70. l.OY]. Typical size: 1/64" to ⅛" [0.4–3.2 mm.]. Shape: Eye-shaped to elongated.

Leaves:

*Size.*—Medium. Average Length: 5½" [140 mm.]. Average Width: 1⅜" [35 mm.].

*Arrangement.*—Alternate.

*Thickness.*—Medium.

*Form.*—Elliptical.

*Apex.*—Acuminate.

*Base.*—Acute to rounded.

*Surface.*—Smooth.

*Color.*—Dorsal Surface: Moderate olive green [125. m. OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: 7/16" [11.1 mm.]. Average Thickness: 1/16" [1.6 mm.]. Color: Moderate yellow green [120. m.YG].

*Stipules.*—Number: 2 per leaf, up to 6 per growing tip. Average Length: ⅛" [3.2 mm.] to 5/16" [7.9 mm.]. Color: Brilliant yellow green [116. brill.YG] becoming Dark yellowish brown [78. d.yBr] with maturity.

*Glands.*—Number: Mostly 2, as many as 4. Position: Alternate, on petiole and base of blade. Size: Medium. Form: Reniform. Color: Brilliant yellow green [116. brill.YG] on the outside with a Dark yellowish brown [78. d.yBr] center.

*Leaf buds.*—Pointed, medium in size.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Strong purplish pink [247. s.pPk].

Flowers: Perfect, complete, perigynous, usually a single pistil, typically thirty or more stamens, five sepals and petal locations alternately positioned.

*Type.*—Showy, very large.

*Average flower diameter.*—1¾" [44.5 mm.].

*Number of petals.*—Usually five, with a small percentage of double blossoms observed.

*Petal shape.*—Circular.

*Petal margin.*—Somewhat wavy.

*Average petal diameter.*—13/16" [20.6 mm.].

*Average petal length.*—13/16" [20.6 mm.].

*Petal apex.*—Rounded, some slightly notched.

*Petal base.*—Rounded.

*Petal color.*—Pale pink [7. p.Pk] toward the apex and Moderate purplish pink [250. m.pPk] toward the base.

*Anther color.*—Deep red [13. deep R] over a Light orange yellow [70. l.OY] center.

*Stigma color.*—Light greenish yellow [101.l.gy].

*Sepal color.*—Dark purplish red [259. d.pR].

*Sepal length.*—5/16" [7.9 mm.].

*Sepal width.*—¼" [6.4 mm.].

*Average pistil length.*—¾" [19.1 mm.]

*Average stamen length.*—9/16" [14.3 mm.]

*Fragrance.*—Moderate.

*Blooming period.*—Medium compared with other varieties.

*Onset of bloom.*—One percent on Mar. 2, 2004.

*Date of full bloom.*—Mar. 12, 2004.

*Duration of bloom.*—One to two weeks, dependent on ambient temperature.

*Number per cluster.*—1 to 3 with single flowers most common.

FRUIT

Maturity when described: Hard ripe, Jul. 17, 2003.

Date of first picking: Jul. 14, 2003.

Date of last picking: Jul. 24, 2003.

Size: Uniform, large.

*Average diameter axially.*—3⅛" [79.4 mm.].

*Average diameter across suture plane.*—3⅛" [79.4 mm.].

*Typical weight.*—9.2 ounces [261 grams].

Form: Globose, uniform.
*Longitudinal section form.*—Circular to slightly oval.
*Transverse section through diameter.*—*Circular.*
Suture: A moderate groove from the stem to somewhat beyond the pistil point that is sharper and deeper toward both the stem cavity and apex with a marked depression beyond the pistil point.
Ventral surface: Rounded, lipped throughout on both sides, stronger toward the apex.
Lips: Slightly unequal.
Cavity: Flaring, elongated in the suture plane, suture showing on one side, Light yellow [86. l.Y] stem markings typical.
*Depth.*—⅝" [15.9 mm.].
*Breadth.*—1" [25.4 mm.].
Base: Rounded to slightly truncate.
Apex: Rounded, but slightly cordate if viewed parallel to the suture.
Pistil point: Some apical and some oblique, negligible in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Slightly astringent.
*Tendency to crack.*—None observed.
*Color.*—Primarily Dark red [16. d.R] over a Strong reddish orange [35. s.rO] background, a slight amount of Light orange yellow [70. l.OY] freckling toward the apex, and occasional small Light yellow [86. l.Y] areas where sun protected.
Flesh:
*Color.*—Brilliant Yellow [83. brill.Y] with Strong red [12. s.R] flecking toward the skin and very near the stone.
*Surface of pit cavity.*—Strong pink [2 s.Pk] fibers breaking when twisted from the stone.
*Amygdalin.*—Moderate.
*Juice.*—Abundant, rich.
*Texture.*—Very firm, crisp.
*Fibers.*—Abundant fine.
*Ripens.*—Slightly earlier at the apex.
*Flavor.*—A tasty blend of acid and sugar, typically 14 brix.
*Aroma.*—Moderate.
*Eating quality.*—Very good.

STONE

Type: Clingstone.
Form: Oval.
Hilum: Narrow, oblong.
Base: Oblique.
Apex: Acute, with an average tip angle of 50 degrees and a length of ⅛" [3.2 mm.].
Sides: Equal.
Surface: Irregularly furrowed and ridged toward the apex, pitted toward the base.
Ridges: Jagged toward the base.
External color: Moderate orange yellow [71. m.OY] when first removed, Moderate brown [58. m.Br] when dry.
Pit wall color when cracked: Light orange yellow [70. l.OY].
Cavity surface color: Light yellowish brown [76. l.yBr].
Average pit wall thickness: ¼" [6.4 mm.]
Average width: 1⅛" [28.6 mm.].
Average length: 1⅝" [41.3 mm.].
Average breadth: ¾ [19.1 mm.].
Tendency to split: Slight.
Kernel:
*Form.*—Oval.
*Skin color.*—Light yellow [86. l.Y] when freshly removed, Strong yellowish brown [74. s.yBr] when dried.
*Pellicle color.*—Grayish yellowish brown [80. gy.yBr].
*Vein color.*—Light grayish yellowish brown [79. l.gy.yBr].
*Taste.*—Sweet.
*Viable.*—Yes.
*Average width.*—⅝" [15.9 mm.].
*Average length.*—⅞" [22.2 mm.].
*Amygdalin.*—Scant.

USE

Market: Fresh market and long distance shipping.
Keeping quality: Good. Fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to its selected seed parent, 'Ruby Diamond' (U.S. Plant Pat. No. 7,918) nectarine, by producing nectarines that are mostly red in skin color, yellow in flesh color, mildly acidic and sweet in flavor, and nearly globose in shape but is determined therefrom by producing nectarines that are clingstone instead of freestone, that are much larger in size, and that mature about seven days later.

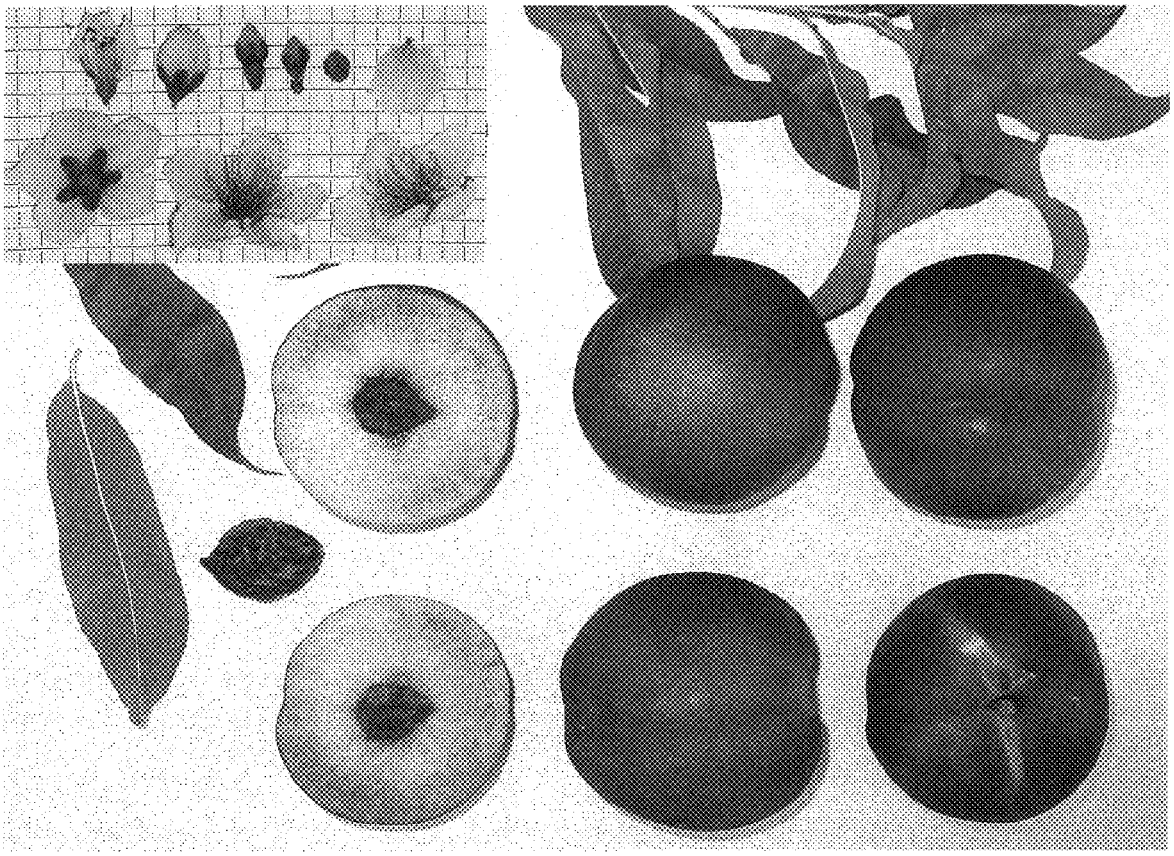

* * * * *